United States Patent
Butler et al.

(10) Patent No.: US 9,616,178 B2
(45) Date of Patent: Apr. 11, 2017

(54) DOSE SETTING MECHANISM AND METHOD OF USING THE SAME

(75) Inventors: Joseph Butler, Rugby (GB); David Plumptre, Droitwich Spa (GB)

(73) Assignee: Sanofi-Aventis Deutschland GmbH, Frankfurt am Main (DE)

(*) Notice: Subject to any disclaimer, the term of this patent is extended or adjusted under 35 U.S.C. 154(b) by 992 days.

(21) Appl. No.: 13/878,113

(22) PCT Filed: Oct. 11, 2011

(86) PCT No.: PCT/EP2011/067678
§ 371 (c)(1),
(2), (4) Date: Jul. 18, 2013

(87) PCT Pub. No.: WO2012/049141
PCT Pub. Date: Apr. 19, 2012

(65) Prior Publication Data
US 2013/0289518 A1    Oct. 31, 2013

Related U.S. Application Data

(60) Provisional application No. 61/392,753, filed on Oct. 13, 2010.

(30) Foreign Application Priority Data

May 31, 2011 (EP) .................................. 11168191

(51) Int. Cl.
*A61M 5/00* (2006.01)
*A61M 5/315* (2006.01)

(52) U.S. Cl.
CPC .... *A61M 5/31535* (2013.01); *A61M 5/31551* (2013.01); *A61M 5/31561* (2013.01);
(Continued)

(58) Field of Classification Search
CPC ...... A61M 2205/581; A61M 2205/582; A61M 2205/584; A61M 2205/585;
(Continued)

(56) References Cited

U.S. PATENT DOCUMENTS 5,092,842 A    3/1992   Bechtold et al.
9,408,979 B2   8/2016   Veasey et al.
(Continued)

FOREIGN PATENT DOCUMENTS

CN    1780652 A      5/2006
JP    2009519074 A   8/2006
(Continued)

OTHER PUBLICATIONS

Form PCT/IPEA/416, Notification of Transmittal of the International Preliminary Report on Patentability.
(Continued)

*Primary Examiner* — Jason Flick
(74) *Attorney, Agent, or Firm* — McDonnell Boehnen Hulbert & Berghoff LLP

(57) ABSTRACT

The present invention relates to a dose setting mechanism for a drug delivery device and a method of using same. The mechanism comprises a drug delivery device housing, a dose dial component positioned in the housing and rotatable during dose setting and dose delivery, a clutch rotatable during dose setting and non-rotatable during dose delivery having, preferably located at a distal end, clutch teeth, and a clutch ring engaged with the housing in a first rotatable configuration and in a second non-rotatable configuration.

15 Claims, 5 Drawing Sheets

(52) U.S. Cl.
CPC ... *A61M 5/31585* (2013.01); *A61M 2205/581* (2013.01); *A61M 2205/582* (2013.01); *A61M 2205/584* (2013.01); *A61M 2205/585* (2013.01)

(58) Field of Classification Search
CPC .......... A61M 5/31535; A61M 5/31551; A61M 5/31561; A61M 5/31585; A61M 5/31553; A61M 5/31583
USPC ........................................................ 604/207
See application file for complete search history.

(56) References Cited

U.S. PATENT DOCUMENTS

| | | |
|---|---|---|
| 2009/0048565 A1 | 2/2009 | Hansen |
| 2009/0275916 A1 | 11/2009 | Harms et al. |
| 2011/0077595 A1* | 3/2011 | Eich .................. A61M 5/31501 604/135 |

FOREIGN PATENT DOCUMENTS

| | | |
|---|---|---|
| JP | 2009518056 A | 5/2009 |
| WO | 9710865 A1 | 3/1997 |
| WO | 2004078239 A1 | 9/2004 |
| WO | 2006114396 A1 | 11/2006 |
| WO | 2009080775 A1 | 7/2009 |
| WO | 2009105908 A1 | 9/2009 |
| WO | 2010072662 A1 | 7/2010 |
| WO | 2010139632 A2 | 12/2010 |
| WO | 2011039163 A1 | 4/2011 |
| WO | 2011039236 A1 | 4/2011 |

OTHER PUBLICATIONS

Office Action issued in Taiwanese Patent Application No. 100136647.

English Translation of Notice of Reasons for Rejection issued in Japanese Patent Application No. 2013-533171 dated Sep. 1, 2015.

* cited by examiner

Table 1

| Dialled Insulin Dose | Pen Number |   |   |   |
|---|---|---|---|---|
|   | 1 | 2 | 3 | 4 |
| 2 | Low | Low | Low | Low |
| 4 | Low | Low | Low | Low |
| 6 | Low | Low | Low | Low |
| 8 | Low | Low | Low | Low |
| 10 | Dose | Low | Low | Low |
| 12 | Dose | Low | Low | Low |
| 14 | Dose | Low | Low | Low |
| 16 | Dose | Low | Low | Low |
| 18 | Dose | Dose | Low | Low |
| 20 | Dose | Dose | Low | Low |
| 22 | Dose | Dose | Low | Low |
| 24 | High | Dose | Low | Low |
| 26 | High | Dose | Low | Low |
| 28 | High | Dose | Low | Low |
| 30 | High | Dose | Low | Low |
| 32 | High | Dose | Low | Low |
| 34 | High | Dose | Low | Low |
| 36 | High | Dose | Low | Low |
| 38 | High | Dose | Dose | Low |
| 40 | High | Dose | Dose | Low |
| 42 | High | Dose | Dose | Low |
| 44 | High | High | Dose | Low |
| 46 | High | High | Dose | Low |
| 48 | High | High | Dose | Low |
| 50 | High | High | Dose | Low |
| 52 | High | High | Dose | Low |
| 54 | High | High | Dose | Low |
| 56 | High | High | Dose | Low |
| 58 | High | High | Dose | Dose |
| 60 | High | High | Dose | Dose |
| 62 | High | High | Dose | Dose |
| 64 | High | High | High | Dose |
| 66 | High | High | High | Dose |
| 68 | High | High | High | Dose |
| 70 | High | High | High | Dose |
| 72 | High | High | High | Dose |
| 74 | High | High | High | Dose |
| 76 | High | High | High | Dose |
| 78 | High | High | High | Dose |
| 80 | High | High | High | Dose |

| Legend | |
|---|---|
| (dotted) | Dose may be dialled and delivered |
| (shaded) | Low Dose - Cannot be dispensed |
| (white) | High dose - Cannot be dialled |

FIG. 6

Table 2

| Dialled Insulin Dose | Pen Number 1 | Pen Number 2 | Pen Number 3 | Pen Number 4 |
|---|---|---|---|---|
| 2  | Dial | Dial | Dial | Dial |
| 4  | Low  | Low  | Low  | Low  |
| 6  | Low  | Low  | Low  | Low  |
| 8  | Low  | Low  | Low  | Low  |
| 10 | Dial | Low  | Low  | Low  |
| 12 | Dial | Low  | Low  | Low  |
| 14 | Dial | Low  | Low  | Low  |
| 16 | Dial | Low  | Low  | Low  |
| 18 | Dial | Dial | Low  | Low  |
| 20 | Dial | Dial | Low  | Low  |
| 22 | Dial | Dial | Low  | Low  |
| 24 | High | Dial | Low  | Low  |
| 26 | High | Dial | Low  | Low  |
| 28 | High | Dial | Low  | Low  |
| 30 | High | Dial | Low  | Low  |
| 32 | High | Dial | Low  | Low  |
| 34 | High | Dial | Low  | Low  |
| 36 | High | Dial | Low  | Low  |
| 38 | High | Dial | Dial | Low  |
| 40 | High | Dial | Dial | Low  |
| 42 | High | Dial | Dial | Low  |
| 44 | High | High | Dial | Low  |
| 46 | High | High | Dial | Low  |
| 48 | High | High | Dial | Low  |
| 50 | High | High | Dial | Low  |
| 52 | High | High | Dial | Low  |
| 54 | High | High | Dial | Low  |
| 56 | High | High | Dial | Low  |
| 58 | High | High | Dial | Dial |
| 60 | High | High | Dial | Dial |
| 62 | High | High | High | Dial |
| 64 | High | High | High | Dial |
| 66 | High | High | High | Dial |
| 68 | High | High | High | Dial |
| 70 | High | High | High | Dial |
| 72 | High | High | High | Dial |
| 74 | High | High | High | Dial |
| 76 | High | High | High | Dial |
| 78 | High | High | High | Dial |
| 80 | High | High | High | Dial |

| Legend | |
|---|---|
| Dial | Dose may be dialled and delivered |
| Low  | Low Dose - Cannot be dispensed |
| High | High dose - Cannot be dialled |

FIG. 7

Table 3

| Dialled Long Acting Insulin Dose | Pen Number | | | | | |
|---|---|---|---|---|---|---|
| | 1 | 2 | 3 | 4 | 5 | 6 |
| | Mix ratio (insulin : GLP-1) | | | | | |
| | 0.83 | 0.665 | 0.53 | 0.43 | 0.35 | 0.285 |
| 2 | | | | | | |
| 4 | | | | | | |
| 6 | | | | | | |
| 8 | | | | | | |
| 10 | | | | | | |
| 12 | | | | | | |
| 14 | | | | | | |
| 16 | | | | | | |
| 18 | | | | | | |
| 20 | | | | | | |
| 22 | 18.3 | | | | | |
| 24 | 19.9 | | | | | |
| 26 | 21.6 | | | | | |
| 28 | | 18.6 | | | | |
| 30 | | 20.0 | | | | |
| 32 | | 21.3 | | | | |
| 34 | | | 18.0 | | | |
| 36 | | | 19.1 | | | |
| 38 | | | 20.1 | | | |
| 40 | | | 21.2 | | | |
| 42 | | | | 18.1 | | |
| 44 | | | | 18.9 | | |
| 46 | | | | 19.8 | | |
| 48 | | | | 20.6 | | |
| 50 | | | | 21.5 | | |
| 52 | | | | | 18.2 | |
| 54 | | | | | 18.9 | |
| 56 | | | | | 19.6 | |
| 58 | | | | | 20.3 | |
| 60 | | | | | 21.0 | |
| 62 | | | | | 21.7 | |
| 64 | | | | | | 18.2 |
| 66 | | | | | | 18.8 |
| 68 | | | | | | 19.4 |
| 70 | | | | | | 20.0 |
| 72 | | | | | | 20.5 |
| 74 | | | | | | 21.1 |
| 76 | | | | | | 21.7 |
| 78 | | | | | | |
| 80 | | | | | | |

| | |
|---|---|
| | GLP-1 Dose - may be dialled and delivered |
| | Low Dose - Cannot be dispensed |
| | High dose - Cannot be dialled |

FIG. 8

DOSE SETTING MECHANISM AND METHOD OF USING THE SAME

CROSS REFERENCE TO RELATED APPLICATIONS

The present application is a U.S. National Phase Application pursuant to 35 U.S.C. §371 of International Application No. PCT/EP2011/067678 filed Oct. 11, 2011, which claims priority to U.S. Provisional Patent Application No. 61/392,753 filed Oct. 13, 2010 and European Patent Application No. 11168191.2 filed May 31, 2011. The entire disclosure contents of these applications are herewith incorporated by reference into the present application.

FIELD OF INVENTION

The present patent application is generally directed to dose setting mechanisms for drug delivery devices that control minimum and/or maximum possible dose settings and a method of using same, e.g. by setting and/or delivering at least a predetermined minimum dose of a medicament. More particularly, the present patent application is generally directed to drug delivery devices, such as pen type drug delivery devices where therapy demands that a patient receive at least a certain minimum dose and not exceed a certain maximum dose of a particular medicament. Such devices provide for self-administration of medicinal product from a multi-dose cartridge and contain dose limiting mechanisms for setting minimum and/or maximum doses. The present application may find application in both disposable and reusable type drug delivery devices. However, aspects of the invention may be equally applicable in other scenarios as well.

BACKGROUND

Self administered injectable medicaments are often delivered using a variable-dose injection device. Such a device is known from WO 2004/078239 A1. Prior to the injection the user selects the dose that they require according to their prescribed dose and/or their current or expected future physical condition. A typical example would be an insulin delivery device for diabetics where a patient's dose is determined according to their prescribed dose and their expected food intake and activity level. Typically such devices allow the user to select any dose from 1 unit up to the maximum units that the device can deliver, typically 60 units or 80 units for a manual device, such as a pen-type or syringe injection device.

The drug delivery device of WO 2004/078239 A1 comprises a housing for receiving a dose setting mechanism, a cartridge, a dose dial sleeve with an attached dose dial grip, a clicker, a drive sleeve, a clutch for coupling and decoupling the dose dial sleeve and the drive sleeve, a rotatable piston rod and a button which is pressed for injecting a set dose. The full description of the pen-type injection devices disclosed in WO 2004/078239 A1 is incorporated herein by reference.

To dial a dose a user rotates the dose dial grip. With the clicker and clutch means engaged, the drive sleeve, the clicker, the clutch means and the dose dial sleeve rotate with the dose dial grip relative to the housing and relative to the piston rod. Audible and tactile feedback of the dose being dialed is provided by the clicker and the clutch means. Torque is transmitted through saw teeth between the clicker and the clutch means.

A helical groove on the dose dial sleeve and a helical groove in the drive sleeve have the same lead. This allows the dose dial sleeve to extend from the housing and the drive sleeve to climb the piston rod at the same rate. At the limit of travel, a radial stop on the dose dial sleeve engages a stop provided on the housing to prevent further movement. Rotation of the piston rod is prevented due to the opposing directions of overhauled and driven threads on the piston rod.

Should a user inadvertently dial beyond the desired dosage, the pen-type injector allows the dosage to be dialed down without dispense of medicinal product from the cartridge. The dose dial grip is counter rotated. This causes the system to act in reverse. The torque transmitted through the clutch means causes the saw teeth to ride over one another to create the clicks corresponding to dialed dose reduction. Preferably the saw teeth are so disposed that the circumferential extent of each saw tooth corresponds to a unit dose.

When the desired dose has been dialed, the user may then dispense this dose by depressing the button. This displaces the clutch means axially with respect to the dose dial sleeve causing dog teeth of the clutch means to disengage. However the clutch means remains keyed in rotation to the drive sleeve. The dose dial sleeve and associated dose dial grip are now free to rotate. The axial movement deforms a flexible part of the clicker to ensure the saw teeth cannot be overhauled during dispense. This prevents the drive sleeve from rotating with respect to the housing though it is still free to move axially with respect thereto. This deformation is subsequently used to urge the clicker and the clutch back along the drive sleeve to restore the connection between the clutch and the dose dial sleeve when pressure is removed from the button. The longitudinal axial movement of the drive sleeve causes the threaded piston rod to rotate through a threaded opening in a housing insert, thereby to advance the piston in the cartridge.

In other words, the drive sleeve moves longitudinally, i.e. only in the axial direction, during an injection. Because the drive sleeve and the piston rod are engaged via corresponding threads on the outer surface of the piston rod and an internal face of the drive sleeve, the longitudinal movement of the drive sleeve causes the piston rod to rotate. The housing insert with the threaded opening which is engaged with the piston rod via corresponding threads is fixed within the housing, i.e. prevented from rotation. Thus, the rotating piston rod is screwed through the threaded opening in the housing insert, i.e. the piston rod performs a combined rotational and longitudinal movement along a helical path defined by the corresponding threads of the threaded opening and the piston rod.

Once the dialed dose has been dispensed, the dose dial sleeve is prevented from further rotation by contact of a plurality of members extending from the dose dial grip with a corresponding plurality of stops formed in the housing, thus determining a zero dose position.

Such pen type drug delivery devices have been designed and developed to perform regular injections by persons without formal medical training. This is increasingly common among patients having diabetes where self-treatment enables such patients to conduct effective management of their disease. Because the patient, and not the health care worker, may be using such a drug delivery device, one requirement is that the device should be robust in construction. The drug delivery device must also be easy to use both in terms of the drug delivery device manipulation and understanding of the device's operation. This is especially true for diabetics who are required to inject themselves repeatedly with insulin solution and the volume of insulin to be injected may vary from patient to patient and even from injection to injection. For at least this reason, certain diabetics may require drug delivery devices that allow the patient to inject successive measured dosages of the same or perhaps different preset volumes of insulin solution accurately and with minimum dexterity challenges. This presents a further design challenge since, in the case of certain diabetics, users may have impaired vision and/or may be physically infirm with limited dexterity.

In addition to insulin, other medicaments require a minimum dose to be delivered before they are therapeutically effective. A variable-dose device that allows the patient to deliver doses below the therapeutically effective minimum dose creates the possibility that the user may deliver the ineffective doses either by an error of dose calculation or by mistakenly selecting the incorrect dose. Likewise, some medicaments require that a maximum dose is not to be exceeded. This may be for safety reasons such as increased risk or severity of side-effects or excessive or unwanted actions of the medicament. Current variable-dose delivery devices typically have a maximum dose that is limited by the maximum dose that the delivery mechanism can provide, however, this does not necessarily relate to the maximum advised or prescribed dose of the medicament.

The present invention has at least two applications. First, is the delivery of a single active medicament which must be a variable dose within a defined dose window, i.e. the dose must be more than a certain minimum dose and must not exceed a certain maximum dose. The second application relates to the delivery of a combined formulation of active medicaments where at least one of the medicaments is preferably delivered as a variable dose and at least one other medicament is preferably delivered as a fixed dose, and where this fixed dose can safely be allowed to vary within a defined dose window, for example by ±10% of the nominal fixed dose.

The minimum and/or maximum dose limited delivery device in accordance with the present invention could be used for a medicament that requires a minimum dose to be delivered before it becomes therapeutically effective, but where a degree of dose adjustment may be required. This dose adjustment may be required for a number of reasons, including tailoring a dose to a patient's body weight or the severity of their medical condition. The minimum and maximum dose limited device (min/max device) may also be used instead of a fully variable (i.e., 0 to max dose) device in order to reduce the possibility for dosing errors by the patient. Using the min/max device rather than a variable dose pen reduces the risk that a patient might accidentally deliver a dose outside the defined dose window, i.e., either too high or too low.

One example of the utility of the min/max device is where a parent could give the min/max delivery device to a child for the child to self-administer and the parent would know that the minimum and maximum levels of the min/max device limited the possible severity of any overdose or under dose. Another example of where such a device might be applicable is for patients who take long acting insulin. Typically a variable dose pen is required when a patient is "titrating" their dose to reach their target blood glucose level. However, once the target blood glucose level has been achieved the dose of long acting insulin typically remains more or less constant over relatively long periods of time. During this period, where their insulin dose is either constant or changes by only a few units on a day-to-day basis, the patient's long acting insulin needs could be effectively met by the minimum and maximum dose limited delivery device.

Table 1 (illustrated in FIG. 6) shows an example family of delivery devices, "Pen 1" through "Pen 4", which could be used in place of a single 1-80 unit variable dose device. Each of the Pens 1-4 are designed and manufactured around the same basic mechanism, but each pen contains either additional or alternative components which are used to set a different minimum and maximum dose. Patients would be prescribed a particular Pen according to their stable long acting insulin dose. For example, according to Table 1 a patient prescribed 30 units per day of long acting insulin would be prescribed Pen 2, which has a minimum dose of 18 units and a maximum dose of 42 units, respectively. Any number of mechanical components can be used in such a pen design to ensure these predetermined min/max doses, including axial and/or rotational stops, detents, clutches, compressible fingers, or the like components.

The insulin dose of diabetic patients may change gradually over time. Therefore there may be a small amount of dose range overlap between Pens to allow for a smooth transition between Pens as the dose increases. For example, according to Table 1 a patient prescribed 40 units per day of long acting insulin would be given Pen 2 if they expected their dose to decrease over time or Pen 3 if they expected their dose to increase over time. The number of pens in the "family" and the selected dose ranges shown in Table 1 are illustrative only. By using the min/max device of the present invention a mistake when selecting the dose is limited to within the pen's operating window. Dialing a dose above or delivering a dose below the pen's dose range would not be possible and this would alert the patient to their error.

The min/max device may also be applicable for the delivery of other medicines, particularly where there is a risk of confusion with similar devices that may lead to dose errors or drug/device mix-ups. One such example would be rapid acting insulin and long acting insulin. Both of these insulins are measured in "units" however the same number of units of each insulin type will have a very different effect and a patient will be prescribed different doses of each drug to be taken at different times throughout the day. A mix up of long acting and rapid acting insulin can cause hypoglycemia and is potentially fatal. Both types of insulin may be delivered by injection pen devices. Patients perform their injections on such a routine basis that an "automatic pilot" effect can occur where patients have been known to mix up their insulin pens, even though the pens are of different design, color, shape and carry different labels.

The presently proposed min/max device may help to prevent this mix up occurring. For example, assume both rapid acting and long acting insulins were each provided with a family of min/max devices according to Table 1. A patient is prescribed 50 units per day of long acting insulin (which would require long acting Pen 3) and 15 units of rapid acting insulin with meals (which would require Pen 1). The most dangerous mix up would occur if the patient mistakenly delivered 50 units of rapid acting insulin rather than long acting insulin. If the patient attempted to do this with the min/max devices then the patient would pick up the rapid insulin device (Pen 1) and find that they could not dial beyond 22 units. This should alert them to the fact that this is not the correct insulin pen, and therefore the incorrect insulin type, and prevent the incorrect insulin being delivered.

The min/max concepts may be applied equally to both disposable devices and reusable devices.

Certain medicines also require the user to perform a "priming" dose to confirm the correct operation of the delivery device and needle. This is usually accomplished by delivering an "air-shot" of 2 units and then checking that the medicine can be seen coming out of the needle. The min/max concept shown in Table 1 would not permit this. If priming functionality is required a second permissible "dose window", for example ranging from 1-2 units, may also be implemented within each pen mechanism. An example of how this could be applied is shown in Table 2 (illustrated in FIG. 7). Although both Tables 1 and 2 show only even numbers of units this is done only for clarity and the device may be configured to deliver odd and even units or potential ½ units.

As mentioned, the presently disclosed devices may also be useful in therapies where the delivery of a combined formulation of active medicaments is needed, where at least one of the medicaments is preferably delivered as a variable dose and at least one other medicament is preferably delivered as a fixed dose. If a patient requires a combination of medicines then there is an advantage if those medicines can be provided as a single formulation (i.e. both drugs are mixed together in predefined proportions and supplied in one primary pack) for delivery by a single injection device in one injection through a single needle. However, if one of the drugs requires the delivery of a user-selectable variable dose and the second drug requires a dose above a minimum dose to be therapeutically effective and must not exceed a given maximum dose, then it is beneficial for the drug delivery device to be configured such that it is prevented from delivering doses that are outside of this range.

For example, a patient may be prescribed a combination therapy of long acting insulin (typically delivered in variable dose devices) and GLP-1 (typically delivered as a fixed dose). GLP-1 is a glucagon-like peptide-1, which is derived from the transcription product of the proglucagon gene and is found in the body where it is secreted by the intestinal L cell as a gut hormone. GLP-1 possesses several physiological properties that make it (and its analogs) a subject of intensive investigation as a potential treatment of diabetes mellitus. In order to avoid the patient having to perform two injections the two medicines are pre-mixed into a single formulation. Since both medicaments are pre-mixed in a fixed ratio it is not possible to vary the long acting insulin dose without also varying the GLP-1 dose. However, it may be acceptable for the GLP-1 dose to vary within a given tolerance, for example ±10%, around a fixed nominal dose. It is therefore possible, using a family of min/max limited devices to provide a family of pre-mix devices which between them will allow delivery of a variable long acting insulin dose and a GLP-1 dose that always falls within ±10% of a given "fixed" dose.

Table 3 illustrated in FIG. 8, for example, shows a family of 6 min/max pen-type injection devices that allow the delivery of any long acting insulin dose from 22-76 units along with a GLP-1 dose that is "fixed" to 20 mg±10%. Each Pen within the family would have different minimum and maximum dose thresholds and would be provided with a primary pack or cartridge of medicament filled with the appropriate mix ratio of the two medicines. The family of pen devices could be provided as disposable mechanical devices, prefilled with the appropriate mix ratio cartridge of medicament. Alternatively, the family of devices could be provided as reusable mechanical devices. In the latter case, the devices would be preferably dedicated to a particular mix ratio cartridge, i.e. only the correct mix ratio cartridge can be loaded into each pen family member.

A third alternative is to provide the "family" of pen devices via a single electronic device that can be programmed with the minimum and maximum dose functionality. Preferably, the min/max electronic device would be loaded with a coded cartridge that would automatically upon being loaded into the device communicate to the device what the required minimum and maximum thresholds should be for that particular cartridge and mix ratio.

One specific means of achieving a minimum settable dose on a variable dose, drug delivery device, such as a pen-type device, is to include a mechanism that prevents dosing of the device until a predetermined minimum dose has been reached. A maximum dose mechanism can also be used with a minimum dose mechanism.

Further, WO 2006/114396 A1 shows an injection device having a coupling member which is rotated as a function of axial displacement. The coupling member is provided with a thread which is engaged by a thread or track on a further member so that the coupling member will be forced to rotate when it is axially displaced. The device known from WO 2006/114396 A1 does neither include a maximum dose mechanism nor a minimum dose mechanism.

SUMMARY

It is an object of the invention to provide a device that reduces or eliminates the risk that a user of an injection device will set and administer a dose below a preselected minimum effective dose of a particular medicament.

This object is solved with a dose setting mechanism as defined in claim 1 and a method as defined in claim 14.

One specific means of achieving a minimum settable dose on a variable dose, drug delivery device, such as a pen-type device, is to include a combined helical and axial clutch path or track that only allows dispensing of the drug compounds after a minimum dose threshold has been reached. This is accomplished by using a clutch ring that has one or more radial protrusions that ride in the path during dose setting and dose delivery. The track of the present invention may be integral to the housing of the dose setting mechanism or may be configured as a separate insert that can be positioned in the housing during assembly or manufacture of the dose setting mechanism. A separate maximum dose mechanism can also be used with a minimum dose mechanism.

According to one possible exemplary embodiment of the present invention a dose setting mechanism for a drug delivery device has a housing, a dose dial component positioned in the housing and rotatable during dose setting and dose delivery. There is also a clutch rotatable during dose setting and non-rotatable during dose delivery having a distal end with clutch teeth. A clutch ring engageable with the clutch engages with the housing in a first rotatable configuration and in a second non-rotatable configuration. If the device has a configuration e.g. similar to that of the device disclosed in WO 2004/078239 A1, rotation of the clutch has to be prevented to allow dose dispensing. Thus, allowing the clutch ring to rotate in its first configuration prevents dose dispensing as long as the clutch ring is in its first rotatable configuration. According to the present invention, the clutch ring is in its first rotatable configuration between a dose 0 and a predefined minimum dose.

Preferably, the clutch ring is engaged with the clutch teeth of the clutch such that relative rotation between the clutch ring and the clutch is allowed during dose setting and relative rotation between the clutch ring and the clutch is prevented during dose dispensing.

The clutch ring can have one or more radial protrusions that engages a combined helical and axial track that is part of the inside of housing or is part of an insert that is affixed or otherwise positioned in the housing during manufacture and/or assembly of the injection device. In a preferred embodiment, during dose setting when the user has set a dose below a predetermined minimum dose, the radial protrusion is in a first path of the track allowing the clutch ring to move helically. When the set dose is equal to or greater than a predetermined minimum dose the radial protrusion is in a second path of the track allowing the clutch ring to move only axially.

Preferably, the dose setting mechanism contains a biasing member, such as a spring, in contact with a distal surface of the clutch ring to cause the clutch ring to engage the clutch teeth on the distal end of the clutch. In a most preferred embodiment the first track path has a helical distance directly proportional to a predetermined minimum set dose. When the radial protrusions of the clutch ring are in the first path of the track, the set dose at such a position cannot be delivered because the helical path will cause the dose dial and clutch to rotate back to the starting position. To prevent the protrusion on the clutch ring from reentering the helical path during dose deliver when the set dose is greater than or equal to the predetermined minimum dose, it is preferred that the mechanism have a non-return member located at a transition point between the first and second paths of the tracks.

To allow the device to deliver an "air shot" or "priming dose" that is below the predetermined minimum deliverable dose, the device can include a second set of helical and axial paths.

Further, the invention also relates to one or more methods of preventing a user from delivering too small a dose of medicament. One such method involves delivering at least a predetermined minimum dose of a medicament comprising setting a dose by rotating a dose dial sleeve in a first direction relative to a device housing, where the sleeve is in clutched engagement with a driver causing the driver and sleeve to move in a proximal axial direction. The method further involves moving a clutch ring in a helical path until a predetermined minimum dose is reached and then having the clutch ring move in an axial path. The dose dial sleeve and clutch are prevented from disengaging when the clutch ring is in the helical path and the dose is less than a predetermined minimum.

A user can manually over-ride the minimum dose function if required by dialing a dose equal to, or greater than, the predetermined minimum dose and then dialing back down to the required dose level. Additionally, the dose count numbers below the minimum dose may be colored a different color such as red to differentiate that the dose dialed is less than the normal minimum dose.

These as well as other advantages of various aspects of our proposed drug delivery device will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 6 illustrates Table 1 showing dialled insulin doses for an example family of delivery devices;

FIG. 7 illustrates Table 2 showing dialled insulin doses for an example family of delivery devices; and FIG. 8 illustrates Table 3 showing dialled insulin doses for an example family of pen-type injection devices.

DETAILED DESCRIPTION

Figure 1:
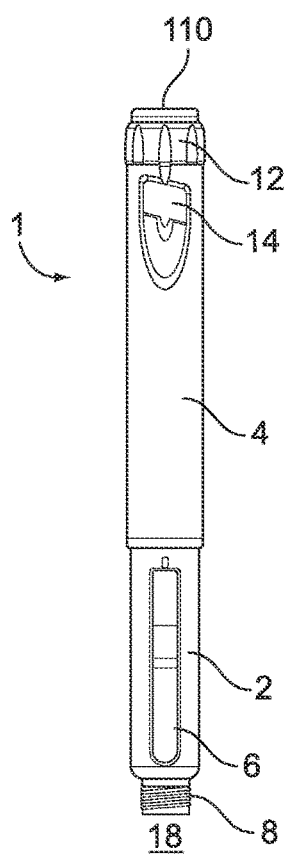
FIG. 1 illustrates a generic design of a pen-type drug delivery device capable of accepting the min/max functionality of the present invention.

Referring to FIG. 1, there is shown a drug delivery device 1 in accordance with an exemplary pen-type design arrangement. The drug delivery device 1 comprises a housing having a first cartridge retaining part 2, and a dose setting mechanism 4. The drug delivery device may be a resettable drug delivery device (i.e., a reusable device) or alternatively a non-resettable drug delivery device (i.e., a non-reusable device). A first end of the cartridge retaining part 2 and a second end of the dose setting mechanism 4 are secured together by connecting features. For non-resettable devices, these connecting features would be permanent and non-reversible. For resettable devices, these connecting features would be releasable.

In this illustrated arrangement, the cartridge retaining part 2 is secured within the second end of the dose setting mechanism 4. A removable cap (not shown) is releasably retained over a second end or distal end of a cartridge retaining part or cartridge housing. The dose setting mechanism 4 comprises a dose dial grip 12 and a window or lens 14. A dose scale arrangement is viewable through the window or lens 14. To set a dose of medication contained within the drug delivery device 1, a user rotates the dose dial grip 12 such that a dialed dose will become viewable in the window or lens 14 by way of the dose scale arrangement.

FIG. 1 illustrates the medical delivery device 1 with the cover cap removed from a distal end 18 of the medical delivery device 1. This removal exposes the cartridge housing 6. Preferably, a cartridge (not shown) from which a number of doses of a medicinal product may be dispensed is provided in the cartridge housing 6. Preferably, the cartridge contains a type of medicament that can be administered relatively often, such as once or more times a day. One such medicament is either long acting or short acting insulin or an insulin analog. The cartridge comprises a bung or stopper that is retained near a second end or a proximal end of the cartridge. The medical delivery device also comprises a driver engaged with a spindle (not illustrated in FIG. 1, but the driver is illustrated as item 106 in FIG. 2). The driver is preferably threadedly engaged a spindle or piston rod. Also part of the drive mechanism, which generally includes the dose dial sleeve, driver, piston rod, is a clutch or other release mechanism (not shown) that directly or indirectly releasably couples the dose dial sleeve to the driver. Preferably, the driver is coupled to the dose dial sleeve during dose setting and uncoupled during dose delivery.

The cartridge housing 6 has a distal end and a proximal end. Preferably, the distal end of the cartridge housing 6 comprises a hub 8 for attaching a removable needle assembly. However, other needle assembly connection mechanisms could also be used. If the drug delivery device 1 comprises a resettable device, the cartridge proximal end is removably connected to the dose setting mechanism 4. In one preferred embodiment, cartridge housing proximal end is removably connected to the dose setting mechanism 4 via a bayonet connection. However, as those of ordinary skill in the art will recognize, other types of removable connection methods such as threads, partial threads, ramps and detents, snap locks, snap fits, and luer locks may also be used.

As previously mentioned, the dose setting mechanism 4 of the drug delivery device illustrated in FIG. 1 may be utilized as a reusable drug delivery device. (i.e., a drug delivery device that can be reset) Where the drug delivery device 1 comprises a reusable drug delivery device, the cartridge is removable from the cartridge housing 6. The cartridge may be removed from the device 1 without destroying the device 1 by merely having the user disconnect the dose setting mechanism 4 from the cartridge housing 6.

In use, once the cap is removed, a user can attach a suitable needle assembly to the hub 8 provided at the distal end of the cartridge housing 6. Such needle assembly may be, for example, screwed onto a distal end of the housing 6 or alternatively may be snapped onto this distal end. After use, the replaceable cap may be used to re-cover the cartridge housing 6. Preferably, the outer dimensions of the replaceable cap are similar or identical to the outer dimensions of the dose setting mechanism 4 so as to provide an impression of a unitary whole when the replaceable cap is in position covering the cartridge housing 6 when the device is not in use.

Figure 2:
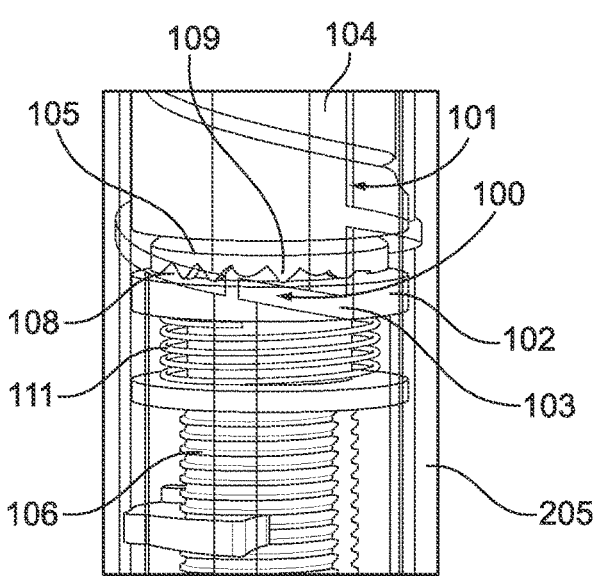
FIG. 2 illustrates a sectional view of a drug delivery device showing one possible embodiment of the dose setting mechanism of the present invention.
Figure 3:
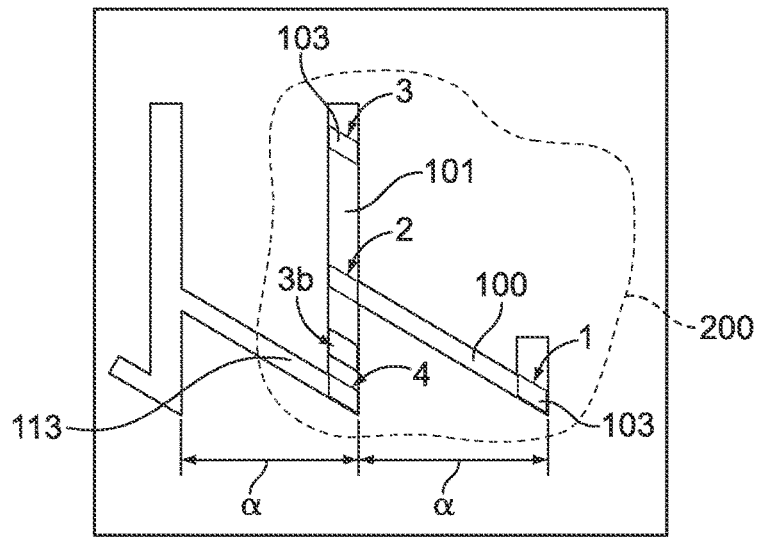
FIG. 3 illustrates a schematic 2D depiction of the track of the embodiment of the dose setting mechanism shown in FIG. 2.

FIG. 2 illustrates a cut-away and enlarged section of the dose setting mechanism 4 having a driver or drive sleeve 106 and dose dial sleeve 104. In this one embodiment the minimum dose limiting function is achieved by means of a combined helical and axial clutch path or track 200 (see FIG. 3) that only allows dispensing of the drug compounds after a minimum dose threshold has been reached. FIG. 3 shows the location 200 of the combined helical and axial clutch path having a helical part 100 and an axial part 101 which are shown preferably on the inside surface of the outer body housing 205 of the dose setting mechanism.

A clutch ring 102 with one or more radial protrusions moves within this track during dose setting and injection. An alternate embodiment of the present invention would incorporate the track into an insert that could be affixed or otherwise added within the outer housing thus making the manufacturing and assembly of the device easier and possibly at a lower cost. The angular position of the start of the axial groove 101 relative to the start of the helical groove 100 determines the predetermined minimum dose that must be dialled before dose delivery is possible. This is shown in FIG. 3 as one half turn of the dose dial sleeve 104 or 180°.

One or more protrusions 103 extending from the clutch ring 102 are engaged into the helical clutch path 100. During setting of a dose, the dial grip 12 is rotated, which in turn causes rotation of the dose dial sleeve 104 and clutch 105. Rotation of the clutch 105 causes rotation of the clutch ring 102 via the diametrically opposed clutch ring teeth 108. After a predetermined rotation of the dial grip 12 the clutch ring protrusion 103 enters the axial section 101 of the combined helical and axial groove or track 200, thereby locking the clutch ring against further rotation relative to the housing, but the dose dial sleeve and clutch can rotate since the clutch ring overrides the teeth and compresses the spring 111 explained below in more detail. As the dialed dose is increased, the clutch ring travels axially in a proximal direction along the axial portion 101 of the helical and axial groove until the required dose is dialled. During this travel, the clutch ring teeth 108 slip over the clutch teeth 109 thereby creating a tactile and audible "click" feedback as each dose increment is dialed. During this stage, the piston rod remains stationary and the drive sleeve 106 rotates with the number sleeve/dose dial sleeve 104.

Figure 4:
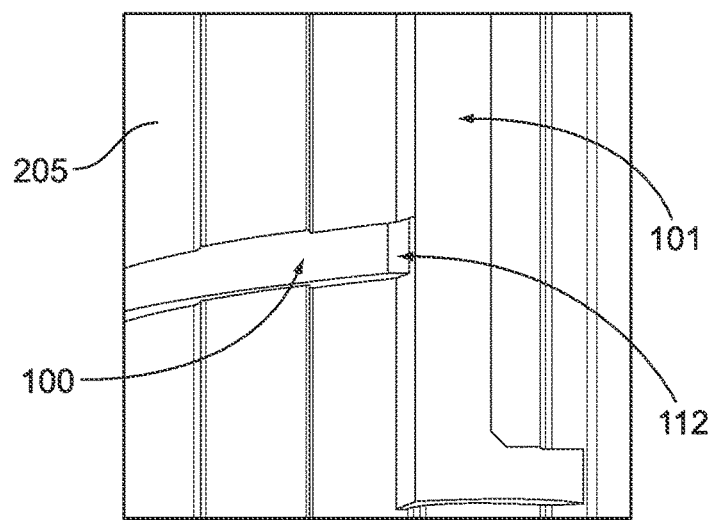
FIG. 4 illustrates a close-up sectional view of the non-return member of the embodiment of the dose setting mechanism shown in FIG. 2.

During dose delivery the dose button 110 is depressed disengaging the clutch 105 from the number sleeve 104 and compressing the biasing member, shown as spring 111, thereby locking the clutch 105 to the clutch ring 102. The number or dose dial sleeve 104 rotates as it returns to its zero dose position, while the clutch ring 102 travels axially in a distal direction down path 101, without rotation and returns to a new position after complete dose delivery. This new position is rotated relative to its original position by an amount equal to the rotation within the helical clutch path 100 and directly proportional to the predetermined minimum dose. A non-return feature 112, as shown in FIG. 4, such as a chamfered pip, located at the interface of paths 100 and 101 of the helical and axial track 200 prevents the clutch ring 102 protrusion 103 from re-entering the helical path 100 of the track 200 as the dose is delivered and the clutch ring instead continues to travel axially in the distal direction down path 101. During dose delivery, the clutch 105 and hence drive sleeve 106 are rotationally locked, and therefore as the dial sleeve 104 is moved towards the zero position with the dose button 110 depressed (dose delivery) the piston rod is forced to rotate and thus advance, thereby delivering the dose.

If the user attempts to deliver a dose below the minimum threshold, the clutch ring protrusion 103 will still be in the helical section 100 of the track 200, and therefore the clutch ring will rotate back down the helical path 100, thereby allowing rotation of the clutch 105 and hence drive sleeve 106 with the end result that a dose is not delivered because the drive sleeve 106 winds back on the piston rod.

FIG. 3 shows a 2D representation of the combined helical and axial track 200. In the particular example shown only two tracks are used so approximates to 180° and equates to the predetermined minimum user dose. However, may equally be 90°, 360°, or some other divisor of 360°. In addition, to changing the dial angle to set the minimum dose limit, the minimum dose limit may also be modified for different medicaments by changing the thread pitch of any of the following: dose dial sleeve 104, inner thread of drive sleeve 106, and/or leadscrew/piston (not shown). FIG. 3 also shows a pictorial representation of each position in the dose setting and delivery process and includes the following:

Position 1: initial zero dose position: Clutch ring 102 radial protrusions 103 are at base of helical groove 100.

Position 2: A minimum dose has been dialled. Clutch ring radial protrusions enter axial section or path 101 of track 200. They have passed the non-return feature 112 and hence cannot re-enter the helical groove 100. However, the clutch has not rotated relative to the clutch ring.

Position 3: The full required dose has been dialled. The clutch ring protrusions have travelled axially in a proximal direction along the axial groove 101 and the clutch has rotated relative to the clutch ring.

Position 4: A dose has been delivered. The clutch ring protrusions have travelled axially in a distal direction along the axial groove 101 back to the start of a second helical groove 113 (or the same helical groove if this path traverses 360°).

Figure 5:
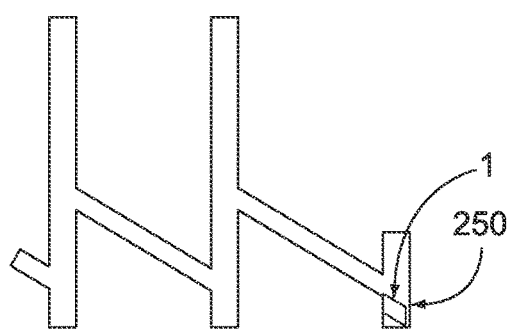
FIG. 5 illustrates a schematic 2D depiction of a track of a further embodiment of the dose setting mechanism of the present invention.

Additional benefits of the present invention include:

a. The "clicker" only operates (i.e., the clutch ring rotates relative to the clutch) after a minimum dose has been dialled. Therefore, providing the user with tactile feedback.

b. A user can manually over-ride the minimum dose function by dialling out to the minimum dose past the non return feature at the end of helical groove 100, and then dialling back down to the required dose level with the clicker operating in the opposite direction. This may be useful if on occasion a user wishes to take a small amount of additional drug. As the user dials back down below the minimum dose threshold the clutch ring radial protrusions will remain in the axial groove section 101 and move to, for example, position 3b. Since the protrusion remains rotationally constrained the "clicker" and clutch will now operate below the minimum dose threshold and it will be possible to deliver doses below the minimum dose.

c. The does dial sleeve may be printed with dose numbers below the minimum dose that are coloured a different colour such as red to differentiate that the dose dialled is less than the normal minimum dose.

d. Alternatively, the device can be configured as shown in FIG. 5 to allow the user to deliver a small priming dose by including a combined axial-helical-axial groove, where the first axial groove 250 allows a prime shot to be delivered.

The embodiment described above is only one of many designs possible, for example, the spring 111 is shown as a coil spring, but it could equally be a flexible washer spring or similar biasing component. Other features such as the clutch ring 102 may also be modified and may fully or partially envelop the spring therefore minimising the required space envelope. As an alternative, the spring 111 may be integrally formed with the clutch ring as a flexible washer spring having clutch ring protrusions 103 and detents or the like members for releasably engaging the clutch teeth.

In a preferred embodiment a master drug compound, such as insulin, contained within a multiple dose, user selectable device could be used with a single use, user replaceable, module that contains a single dose of a secondary medicament and the single dispense interface. When connected to the primary device, the secondary compound is activated/delivered on dispense of the primary compound. Although the present application specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our invention.

For the purposes of our invention the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys(B3), Glu(B29) human insulin; Lys(B28), Pro (B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta¬ decanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

Exemplary embodiments of the present drug delivery device have been described. Those skilled in the art will understand, however, that changes and modifications may be made to these embodiments without departing from the true scope and spirit of the presently proposed drug delivery device, which is defined by the claims.

The invention claimed is:

1. A dose setting mechanism for a drug delivery device, the mechanism comprising:
    a drug delivery device housing;
    a dose dial sleeve positioned in the housing and rotatable during dose setting and dose delivery,
    a clutch rotatable during dose setting and non-rotatable during dose delivery, wherein the clutch releasably couples the dose dial sleeve to a driver during dose setting and uncouples the dose dial sleeve and the driver during dose delivery; and
    a clutch ring, which is engageable with the clutch and which is engaged with the housing in a first rotatable configuration until a predetermined minimum dose is reached and in a second non-rotatable configuration, wherein allowing the clutch ring to rotate in its first rotatable configuration prevents dose dispensing.

2. The mechanism of claim 1, wherein the clutch has clutch teeth located at a distal end thereof, wherein the clutch ring is engaged with the clutch teeth of the clutch such that relative rotation between the clutch ring and the clutch is allowed during dose setting and relative rotation between the clutch ring and the clutch is prevented during dose dispensing.

3. The mechanism of claim 1, wherein rotation of the clutch relative to the housing prevents dispensing of a set dose.

4. The mechanism of claim 1, wherein the clutch ring has a radial protrusion that engages a combined helical and axial track in the housing.

5. The mechanism of claim 4, wherein during dose setting below a predetermined minimum dose the radial protrusion is in a first path of the track allowing the clutch ring to move helically.

6. The mechanism of claim 4, wherein during dose setting equal to or greater than a predetermined minimum dose the radial protrusion is in a second path of the track allowing the clutch ring to move only axially.

7. The mechanism of claim 1, further comprising a biasing member in contact with a distal surface of the clutch ring.

8. The mechanism of claim 5, wherein the first track path has a helical distance directly proportional to a predetermined minimum set dose.

9. The mechanism of claim 5, wherein a set dose cannot be delivered when the radial protrusion is in the first path of the track.

10. The mechanism of claim 5, further comprising a non-return member located at a transition point between the first and second paths of the tracks.

11. The mechanism of claim 4, wherein the combined helical and axial paths of the track comprises an insert that can be affixed inside the housing during device assembly.

12. The mechanism of claim 4 where the clutch ring is engaged with clutch teeth formed on the clutch in a first non-rotatable configuration, a second rotatable configuration and in a third non-rotatable configuration, and wherein the combined helical and axial paths of the track is configured to allow priming dose to be set and expelled from the device, such that the priming dose is less than a predetermined minimum dose.

13. The mechanism of claim 1, wherein clutch ring is integrally formed with a flexible washer spring having clutch ring protrusions and clutch ring teeth for releasably engaging clutch teeth formed on the clutch.

14. A method of delivering at least a predetermined minimum dose of a medicament comprising:
setting a dose by rotating a dose dial sleeve in a first direction relative to a device housing, wherein the dose dial sleeve is in clutched engagement with a driver causing the driver and the dose dial sleeve to move in a proximal axial direction;
moving a clutch ring in a helical path until a predetermined minimum dose is reached and then having the clutch ring move in an axial path), wherein the clutch ring engages a clutch in a rotatable manner during dose setting and engages the clutch in a non-rotatable manner during dose dispensing.

15. The method of claim 14, wherein dispensing of a set dose is prevented when the clutch ring is in the helical path and the dose is less than the predetermined minimum dose.

* * * * *